(12) United States Patent
Chang et al.

(10) Patent No.: US 7,122,500 B2
(45) Date of Patent: Oct. 17, 2006

(54) MOLECULAR SIEVE CATALYST COMPOSITION, ITS MAKING AND USE IN CONVERSION PROCESSES

(75) Inventors: Yun-Feng Chang, Houston, TX (US); Luc R. Martens, Meise (BE); Stephen N. Vaughn, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 244 days.

(21) Appl. No.: 10/668,493

(22) Filed: Sep. 22, 2003

(65) Prior Publication Data

US 2005/0065021 A1    Mar. 24, 2005

(51) Int. Cl.
   *B01J 29/06*    (2006.01)
(52) U.S. Cl. .................. 502/214; 502/64; 502/208
(58) Field of Classification Search ................. 502/60, 502/64, 208, 214; 423/306
   See application file for complete search history.

(56) References Cited

U.S. PATENT DOCUMENTS

| | | | |
|---|---|---|---|
| 3,902,993 A * | 9/1975 | Houser et al. .............. 209/166 |
| 4,062,905 A | 12/1977 | Chang et al. |
| 4,079,095 A | 3/1978 | Givens et al. |
| 4,299,733 A | 11/1981 | Tu ............................. 252/455 |
| 4,310,440 A | 1/1982 | Wilson et al. |
| 4,440,871 A | 4/1984 | Lok et al. |
| 4,474,741 A | 10/1984 | Hoelderich et al. .......... 423/329 |
| 5,051,164 A * | 9/1991 | Herbst et al. .......... 208/120.15 |
| 5,063,187 A | 11/1991 | Burgfels et al. .............. 502/71 |
| 5,168,084 A | 12/1992 | Pellet et al. .................... 502/9 |
| 5,316,656 A | 5/1994 | Pellet et al. ................. 208/120 |
| 5,320,773 A * | 6/1994 | Perman et al. .............. 252/191 |
| 5,367,100 A | 11/1994 | Gongwei et al. |
| 5,525,323 A | 6/1996 | Mueller et al. .............. 423/705 |
| 5,824,835 A * | 10/1998 | Agaskar et al. ............. 585/722 |
| 5,919,721 A * | 7/1999 | Potter .......................... 502/64 |
| 6,153,552 A * | 11/2000 | Wachter et al. ............. 502/208 |
| 6,503,863 B1 | 1/2003 | Fung et al. |
| 6,541,415 B1 | 4/2003 | Vaughn et al. |
| 6,746,660 B1 * | 6/2004 | Chiang et al. .............. 423/702 |
| 2003/0018228 A1 | 1/2003 | Vaughn et al. |
| 2003/0018229 A1 | 1/2003 | Vaughn et al. |
| 2003/0181322 A1 | 9/2003 | Chang et al. |

FOREIGN PATENT DOCUMENTS

| | | |
|---|---|---|
| EP | 0448 000 | 3/1991 |
| WO | WO 03/000413 | 1/2003 |
| WO | WO 2003/000412 | 3/2003 |

OTHER PUBLICATIONS

Abstract of SU 1472447, "Prepn. of high-silica zeolite with increased crystallinity", Apr. 15, 1989.
Abstract of RU 2173299, "Production of a phosphated crystalline aluminum oxide", Sep. 10, 2001.
Abstracts of JP 6048725 and JP 3303341, "Prodn. of beta-type zeolite—by heating mixt. Contg. Silica source, alumina source, alkali source, template agent and water in closed container", Feb. 22, 1994 and Jul. 22, 2002, respectively.
Abstract of Su 1558456, "Sepn. of heterogeneous catalyst for hydrogenation of fatty acids", Apr. 23, 1990.
Abstract of "Sorption and catalytic reaction in silicoaluminates and silicoborates of the pentasil class", BMFT-FB-T 82-175, 34 pp. (1982).
Hammon, U. et al., "Formation of Ethene and Propane from Methanol on Zeolite ZSM-5", Applied Catalysis, vol. 37, pp. 155-174 (1988).
Robson, H. et al., "Verified Synthesis of Zeolitic Materials, second revised edition", 2001, Elsevier Science B.V. Amsterdam, XP-002276929.

* cited by examiner

*Primary Examiner*—David Sample

(57) ABSTRACT

The invention relates to a molecular sieve catalyst composition, to a method of making or forming the molecular sieve catalyst composition, and to a conversion process using the catalyst composition. In particular, the invention is directed to making a formulated molecular sieve catalyst composition with a synthesized molecular sieve having been recovered using a flocculant. The formulated composition is particularly useful in a conversion process for producing olefin(s), preferably ethylene and/or propylene, from a feedstock, preferably an oxygenate containing feedstock.

18 Claims, No Drawings

MOLECULAR SIEVE CATALYST COMPOSITION, ITS MAKING AND USE IN CONVERSION PROCESSES

FIELD OF THE INVENTION

The present invention relates to a molecular sieve catalyst composition, to a method of making or forming the molecular sieve catalyst composition, and to a conversion process using the catalyst composition.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstock. Ethylene and propylene are important commodity petrochemicals useful in a variety of processes for making plastics and other chemical compounds.

The petrochemical industry has known that oxygenates, especially alcohols, are convertible into light olefin(s). There are numerous technologies available for producing oxygenates including fermentation or reaction of synthesis gas derived from natural gas, petroleum liquids, carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Syngas production processes are well known, and include conventional steam reforming, autothermal reforming, or a combination thereof.

Methanol, the preferred alcohol for light olefin production, is typically synthesized from the catalytic reaction of hydrogen, carbon monoxide and/or carbon dioxide in a reactor in the presence of a heterogeneous catalyst. For example, in one synthesis process methanol is produced using a copper/zinc oxide catalyst in a water-cooled tubular reactor. The preferred methanol conversion process is generally referred to as a methanol-to-olefin(s) process (MTO), where an oxygenate, typically mostly methanol, is converted into primarily ethylene and/or propylene in the presence of a molecular sieve.

There are many different types of molecular sieves well known to convert a feedstock, especially an oxygenate containing feedstock, into one or more olefin(s). Molecular sieves, such as zeolites or zeolite-type molecular sieves, carbons and oxides, are porous solids having pores of different sizes that selectively adsorb molecules that can enter the pores, and exclude other molecules that are too large. Examples of molecular sieves useful in converting an oxygenate into olefin(s) are: U.S. Pat. No. 5,367,100 describes the use of a well known zeolite, ZSM-5, to convert methanol into olefin(s); U.S. Pat. No. 4,062,905 discusses the conversion of methanol and other oxygenates to ethylene and propylene using crystalline aluminosilicate zeolites, for example Zeolite T, ZK5, erionite and chabazite; U.S. Pat. No. 4,079,095 describes the use of ZSM-34 to convert methanol to hydrocarbon products such as ethylene and propylene; U.S. Pat. No. 4,310,440 describes producing light olefin(s) from an alcohol using a crystalline aluminophosphates, often represented by $ALPO_4$; and U.S. Pat. No. 4,440,871 describes silicoaluminophosphate molecular sieves (SAPO), one of the most useful molecular sieves for converting methanol into olefin(s).

Typically, molecular sieves are formed into molecular sieve catalyst compositions to improve their durability in commercial conversion processes. The collisions within a commercial process between catalyst composition particles themselves, the reactor walls, and other reactor systems cause the particles to breakdown into smaller particles called fines. The physical breakdown of the molecular sieve catalyst composition particles is known as attrition. Problems develop in the recovery systems because fines often exit the reactor in the product containing effluent stream. Catalyst compositions having a higher resistance to attrition generate fewer fines; this results in improved process operability, and less catalyst composition being required for a conversion process, and therefore, lower overall operating costs.

It is known that the way in which the molecular sieve catalyst compositions are made or formulated affects catalyst composition attrition. Molecular sieve catalyst compositions are formed by combining a molecular sieve and a matrix material usually in the presence of a binder. For example, PCT Patent Publication WO 03/000413 A1 published Jan. 3, 2003 discloses a low attrition molecular sieve catalyst composition using a synthesized molecular sieve that has not been fully dried, or partially dried, in combination in a slurry with a matrix material and/or a binder. Also, PCT Patent Publication WO 03/000412 A1 published Jan. 3, 2003 discusses a low attrition molecular sieve catalyst composition produced by controlling the pH of the slurry above the isoelectric point of the molecular sieve. U.S. Patent Application Publication No. US 2003/0018228 published Jan. 23, 2003 shows making a low attrition molecular sieve catalyst composition by making a slurry of a synthesized molecular sieve, a binder, and optionally a matrix material, wherein 90 percent by volume of the slurry contains particles having a diameter less than 20 μm. U.S. patent application Ser. No. 10/178,455 filed Jun. 24, 2002, which is herein fully incorporated by reference, illustrates making an attrition resistant molecular sieve catalyst composition by controlling the ratio of a binder to a molecular sieve. U.S. Pat. No. 6,503,863 is directed to a method of heat treating a molecular sieve catalyst composition to remove a portion of the template used in the synthesis of the molecular sieve. U.S. Pat. No. 6,541,415 describes improving the attrition resistance of a molecular sieve catalyst composition that contains molecular sieve-containing recycled attrition particles and virgin molecular sieve and having been calcined to remove the template from the molecular sieve catalyst.

It is also known that in typical commercial processes that flocculants are used in the recovery of synthesized molecular sieves. These flocculants are known to facilitate the crystal recovery and to increase the yield of recovery of the synthesized molecular sieve typically in a large scale commercial process. However, the presence of a flocculate can affect the catalyst formulation, and in some cases flocculation can result in the formulation of catalyst compositions having lower attrition resistance.

Although these molecular sieve catalyst compositions described above are useful in hydrocarbon conversion processes, it would be desirable to have an improved molecular sieve catalyst composition having better attrition resistance and commercially desirable operability, and cost advantages.

SUMMARY OF THE INVENTION

This invention generally provides for a method of making or formulating a molecular sieve catalyst composition and to its use in a conversion process for converting a feedstock into one or more olefin(s).

In one embodiment the invention is directed to a method for formulating a molecular sieve catalyst composition, the method comprising the steps of: (a) providing a synthesized molecular sieve having been recovered in the presence of a flocculant; (b) thermally treating the synthesized molecular sieve; (c) making a slurry of the thermally treated synthesized molecular sieve, a binder, and optionally a matrix material, (d) forming the slurry to produce a formulated molecular sieve catalyst composition. In a preferred embodiment, the synthesized molecular sieve is synthesized from a synthesis mixture comprising one or more, preferably two or more, most preferably three or more of a silicon source, a phosphorous source and an aluminum source, optionally in the presence of a templating agent. In a most preferred embodiment, the slurry in step (d) is formed by spray drying, and then optionally, the spray dried formulated molecular sieve catalyst composition is calcined. Preferably the synthesized molecular sieve is a metallo-aluminophosphate, a silicoaluminophosphate, an aluminophosphate, a chabazite (CHA) framework-type molecular sieve, or a CHA and AEI intergrowth or mixed framework-type molecular sieve. Also, in a preferred embodiment of any of the above embodiments, the amount of synthesized molecular sieve provided in step (a) is greater than 250 Kg, preferably greater than 500 Kg, and most preferably greater than about 1000 Kg.

In another preferred embodiment, the invention relates to a method for synthesizing a molecular sieve, the method comprising the steps of: (a) crystallizing the molecular sieve in a slurry, the slurry comprising one or more of a silicon source, an aluminum source, a phosphorous source and a templating agent; (b) contacting a flocculant with the molecular sieve; (c) recovering the molecular sieve; and (d) heat treating the molecular sieve, preferably at a temperature in the range of from about 50° C. to about 250° C., more preferably from about 90° C. to about 180° C., and most preferably from about 100° C. to about 160° C. In a preferred embodiment of this embodiment, the slurry comprises a silicon source, an aluminum source, a phosphorous source and a templating agent. In another preferred embodiment, in step (c), the molecular sieve is recovered by filtration. In yet another preferred embodiment, the amount of molecular sieve recovered is greater than 250 Kg, preferably greater than 500 Kg, and most preferably greater than 1000 Kg.

In yet another embodiment of the invention, the invention is directed to a method for formulating a molecular sieve catalyst composition, the method comprising the step of: (A) synthesizing a molecular sieve in a reaction vessel, the synthesizing method of step (A) comprising the steps of: (a) crystallizing the molecular sieve in a synthesis mixture; (b) settling the molecular sieve in a vessel by introducing a flocculant to the synthesis mixture; (c) recovering the molecular sieve; (d) thermally treating the molecular sieve; and (B) combining the thermally treated molecular sieve with a binder and a matrix material to form the molecular sieve catalyst composition. In this embodiment, it is preferred that the molecular sieve in step (c) is recovered by filtering the synthesis mixture. It also preferred that prior to step (c) that a portion of a liquid in the synthesis mixture is separated from the molecular sieve, and additional flocculant and/or liquid, preferably water, are introduced to the synthesis mixture. In the most preferred embodiment the molecular sieve catalyst composition is calcined after step (B). Lastly, in another preferred embodiment of any of the above embodiments, the reactor vessel is capable of producing greater than 250 Kg, preferably greater than 500 Kg, more preferably greater than 1000 Kg or more molecular sieve in a single batch.

In yet another embodiment, the invention is directed to a process for producing olefin(s) in the presence of any of the above synthesized molecular sieves or formulated molecular sieve catalyst compositions. In particular, the process involves producing olefin(s) in a process for converting a feedstock, preferably a feedstock containing an oxygenate, more preferably a feedstock containing an alcohol, and most preferably a feedstock containing methanol in the presence of one or more of the formulated molecular sieve catalyst compositions discussed above.

DETAILED DESCRIPTION OF THE INVENTION

Introduction

The invention is directed toward a molecular sieve catalyst composition, its making, and to its use in the conversion of a feedstock into one or more olefin(s). A formulated molecular sieve catalyst composition is typically formed from a slurry of the combination of a molecular sieve, a matrix material, and optionally, most preferably, a binder. It has been discovered that when recovering a molecular sieve in the presence of a flocculant in a molecular sieve synthesis process, the synthesized molecular sieve when thermally treated prior to formulation with a matrix material, and optionally a binder, maintains or improves its resistance to attrition in various conversion processes.

Molecular Sieves

Molecular sieves have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite Framework Types,* 5th edition, Elsevier, London, England (2001), which is herein fully incorporated by reference. For additional information on molecular sieve types, structures and characteristics, see van Bekkum, et al., *Introduction to Zeolite Science and Practice, Second Completely Revised and Expanded Edition,* Volume 137, Elsevier Science, B. V., Amsterdam, Netherlands (2001), which is also fully incorporated herein by reference.

Non-limiting examples of these molecular sieves are the small pore molecular sieves, AEI, AFT, APC, ATN, ATT, ATV, AWW, BIK, CAS, CHA, CHI, DAC, DDR, EDI, ER1, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEI, AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably an intergrowth thereof.

The small, medium and large pore molecular sieves have from a 4-ring to a 12-ring or greater framework-type. In a preferred embodiment, the molecular sieves have 8-, 10- or 12-ring structures or larger and an average pore size in the range of from about 3 Å to 15 Å. In the most preferred embodiment, the molecular sieves, preferably a SAPO molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves based on silicon, aluminum, and phosphorous, and metal containing molecular sieves thereof, have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500, 651, 4,551,236 and 4,605,492 (TiAPO), U.S. Pat. Nos. 4,824,554, 4,744,970 (CoAPSO), U.S. Pat. No. 4,735,806 (GAAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,098,684 (MCM-41), U.S. Pat. No. 5,198,203 (MCM-48), U.S. Pat. Nos. 5,241,093, 5,304,363 (MCM-50), U.S. Pat. Nos. 5,493,066, 5,675,050, 6,077,498 (ITQ-1), U.S. Pat. No. 6,409,986 (ITQ-5), U.S. Pat. No. 6,419,895 (UZM-4), U.S. Pat. No. 6,471,939 (ITQ-12), U.S. Pat. No. 6,471,941 (ITQ-13), U.S. Pat. No. 6,475,463 (SSZ-55), U.S. Pat. No. 6,500, 404 (ITQ-3), U.S. Pat. No. 6,500,998 (UZM-5 and UZM-6), U.S. Pat. No. 6,524,551 (MCM-58) and U.S. Pat. No. 6,544,495 (SSZ-57), U.S. Pat. No. 6,547,958 (SSZ-59), U.S. Pat. No. 6,555,090 (ITQ-36) and U.S. Pat. No. 6,569,401 (SSZ-64), all of which are herein fully incorporated by reference. Other molecular sieves are described in R. Szostak, *Handbook of Molecular Sieves*, Van Nostrand Reinhold, New York, N.Y. (1992), which is herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves.

In one embodiment, the molecular sieve, as described in many of the U.S. Patents mentioned above, is represented by the empirical formula, on an anhydrous basis:

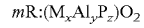

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Synthesis of a molecular sieve, especially a SAPO molecular sieve, its formulation into a SAPO catalyst, and its use in converting a hydrocarbon feedstock into olefin(s), is shown in, for example, U.S. Pat. Nos. 4,499,327, 4,677, 242, 4,677,243, 4,873,390, 5,095,163, 5,714,662 and 6,166, 282, all of which are herein fully incorporated by reference. Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, SAPO intergrowth molecular sieves are described in the U.S. patent application Ser. No. 09/924,016 filed Aug. 7, 2001, PCT Publication WO 02/070407 published Sep. 12, 2002 and PCT Publication WO 98/15496 published Apr. 16, 1998, which are herein fully incorporated by reference. For example, SAPO-18, ALPO-18 and RUW-18 have an AEI framework-type, and SAPO-34 has a CHA framework-type. In another embodiment, the molecular sieve comprises at least one intergrown phase of AEI and CHA framework-types, preferably the molecular sieve has a greater amount of CHA framework-type to AEI framework-type, and more preferably the molar ratio of CHA to AEI is greater than 1:1.

Molecular Sieve Synthesis

Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds, and are placed in a sealed pressure vessel, optionally lined with an inert plastic such as polytetrafluoroethylene, and heated, under a crystallization pressure and temperature, until a crystalline material is formed in a synthesis mixture. Then, in a commercial process in particular, one or more flocculant(s) is added to the synthesis mixture. The crystalline molecular sieve material settles within the reactor vessel. A liquid portion of the synthesis mixture is removed, decanted, or reduced in quantity. The remaining synthesis mixture containing the crystalline molecular sieve is then, optionally, contacted with the same or a different fresh liquid, typically with water, from once to many times depending on the desired purity of the supernatant, liquid portion, of the synthesis mixture being removed, a washing step. It is also optional to repeat this process by adding in additional flocculant followed by additional washing steps. Then, the crystallized molecular sieve is recovered by filtration, centrifugation and/or decanting. Preferably, the molecular sieve is filtered using a filter that provides for separating certain crystal sized molecular sieve particles from any remaining liquid portion that may contain different size molecular sieve crystals.

In a preferred embodiment the molecular sieves are synthesized by forming a reaction product or synthesis mixture of a source of silicon, a source of aluminum, a source of phosphorous and an organic templating agent, preferably a nitrogen containing organic templating agent. This particularly preferred embodiment results in the synthesis of a silicoaluminophosphate crystalline material in a synthesis mixture. One or more flocculants are added to the synthesis mixture, and the crystallized molecular sieve is then removed or isolated by filtration, centrifugation and/or decanting.

Non-limiting examples of silicon sources include a silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as $ALPO_4$, phosphorous salts, or combinations thereof. The preferred source of phosphorous is phosphoric acid, particularly when producing a silicoaluminophosphate.

Templating agents are generally compounds that contain elements of Group VA of the Periodic Table of Elements, particularly nitrogen, phosphorus, arsenic and antimony, more preferably nitrogen or phosphorous, and most preferably nitrogen. Typical templating agents of Group VA of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula $R_4N^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof. The preferred templating agent or template is a tetraethylammonium compound, tetraethyl ammonium hydroxide (TEAOH) and salts thereof, particularly when producing a SAPO molecular sieve.

Flocculants

When commercially synthesizing any of the molecular sieves discussed above, typically one or more chemical reagents are added to the crystallization vessel or synthesis reactor after crystallization is substantially, preferably complete. Optionally, in another embodiment, the synthesis mixture is transferred to another vessel separate from the reaction vessel or the vessel in which crystallization occurs, and a flocculant is then added to this other vessel from which the crystalline molecular sieve is ultimately recovered. These chemical reagents or flocculants are used to increase the recovery rate of the molecular sieve crystals and increase the yield of the synthesized molecular sieve crystals. While not wishing to be bound to any particular theory, these flocculants act either as (1) a surface charge modifier that results in the agglomeration of very small crystals into larger aggregates of molecular sieve crystals; or (2) surface anchors that bridge many small crystals to form aggregates of molecular sieve crystals. The aggregates of the molecular sieve crystals are then easily recovered by well known techniques such as filtration or through a filter press process.

Flocculants can be added at any point during or with any other source or templating agent used in the synthesis of any one of the molecular sieves discussed above. In one embodiment, flocculants are added to a molecular sieve synthesis mixture comprising one or more of a silicon source, a phosphorous source, an aluminum source, and a templating agent depending on the molecular sieve being synthesized. In the most preferred embodiment, the flocculant is added to the synthesis mixture after crystallization has occurred from the combination of one or more of a silicon source, a phosphorous source, an aluminum source, and a templating agent. The synthesized molecular sieve is then recovered by filtration, however, optionally, the synthesized molecular sieve is washed and additional flocculant is used to further aggregate any remaining synthesized molecular sieve from the liquid portion of the synthesis mixture.

There are many types of flocculants both inorganic and organic flocculants. Inorganic flocculants are typically aluminum or iron salts that form insoluble hydroxide precipitates in water. Non-limiting examples such as alum, poly (aluminum chloride), sodium aluminate, iron (III)-chloride, sulfide, and sulfate-chloride, iron (II) sulfate, and sodium silicate (activated silica). The major classes of flocculants used in industry are: (1) nonionic flocculant, for example, polyethylene oxide, polyacrylamide (PAM), partially hydrolyzed polyacrylamide (HPAM), and dextran; (2) cationic flocculant, for example, polyethyleneimine, polyacrylamide-co-trimethylammonium, ethyl methyl acrylate chloride (PTAMC), and poly(N-methyl-4-vinylpyridinium iodide); and (3) anionic flocculant, for example, dextran sulfates, alum (aluminum sulfate), and/or high molecular weight ligninsulfonates prepared by a condensation reaction of formaldehyde with ligninsulfonates, and polyacrylamide. In a preferred embodiment, where the synthesis mixture includes the presence of water, it is preferable that the flocculant used is water soluble. Additional information on flocculation is discussed in T. C. Patton, *Paint Flow and Pigment Dispersion—A Rheological Approach to Coating and Ink Technology*, 2nd Edition, John Wiley & Sons, New York, p. 270, 1979, which is fully incorporated by reference.

A synthesis mixture comprising a molecular sieve and a flocculant should have a pH in the range of from 2 to 10, preferably in the range of from 4 to 9, and most preferably in the range of from 5 to 8. Generally, the synthesis mixture is sealed in a vessel and heated, preferably under autogenous pressure, to a temperature in the range of from about 80° C. to about 250° C., and more preferably from about 150° C. to about 180° C. The time required to form the crystalline molecular sieve is typically from immediately up to several weeks, the duration of which is usually dependent on the temperature; the higher the temperature the shorter the duration. Typically, the crystalline molecular sieve product is formed, usually in a slurry state, and then a flocculant is introduced to this slurry, the synthesis mixture. The crystalline molecular sieve is then recovered by any standard technique well known in the art, for example centrifugation or filtration. Alternatively, in another embodiment, the flocculant is introduced into the synthesis mixture directly.

Determination of the percentage of liquid or liquid medium and the percentage of flocculent and/or template for purposes of this patent specification and appended claims uses a Thermal Gravimetric Analysis (TGA) technique as follows: An amount of a molecular sieve material, the sample, is loaded into a sample pan of a Cahn TG-121 Microbalance, available from Cahn Instrument, Inc., Cerritos, Calif. During the TGA technique, a flow of 114 cc/min (STP) air was used. The sample is then heated from 25° C. to 180° C. at 30° C./min, held at 180° C. for 3 hours or until the weight of this sample becomes constant. The weight loss the percentage to the starting molecular sieve material is then treated as the percentage of the liquid or liquid medium. Subsequently, the sample is heated at 30° C./min from 180° C. to 650° C. and held at 650° C. for 2 hours. This weight loss as a percentage of the original sample weight during this treatment is regarded as the weight loss of the templating agent. The total weight loss as a percentage in terms of the original first sample weight during this entire TGA treatment is defined as Loss-On-Ignition (LOI).

In one embodiment, the isolated or separated crystalline product, the synthesized molecular sieve, is washed, typically using a liquid such as water, from one to many times, or in a semi-continuous or continuous way for variable lengths of time. The washed crystalline product is then optionally dried, preferably in air to a level such that the resulting, partially dried or dried crystalline product or synthesized molecular sieve has a LOI in the range of from about 0 weight percent to about 80 weight percent, preferably the range is from about greater than 1 weight percent to about 80 weight percent, more preferably from about 10 weight percent to about 70 weight percent, even more preferably from about 20 to about 60 weight percent, and most preferably from about 40 weight percent to about 60 weight percent. This liquid containing crystalline product, synthesized molecular sieve or wet filtercake, is then used below in the formulation of the molecular sieve catalyst composition of the invention.

It has been discovered that at least a portion of the flocculant remains in the washed crystalline product, synthesized molecular sieve, or wet filtercake described above. In one embodiment, the crystalline product, synthesized molecular sieve, or wet filtercake comprising a flocculant is thermally treated or heat treated to remove a portion or all of the flocculant. In a preferred embodiment, a synthesized molecular sieve comprising a flocculant is heated to a temperature in the range of from 25° C. to less than a calcination temperature of from about 450° C. or higher.

In one embodiment, the heat treated or thermally treated synthesized molecular sieve comprising a flocculant and optionally a templating agent, or wet filter cake comprising a flocculant and a templating agent, is heated to a temperature in the range of from about 50° C. to about 250° C., more preferably in the range of from about 75° C. to about 200° C., and even more preferably in the range of from about 90° C. to about 180° C., and most preferably in the range of from about 100° C. to about 160° C. Depending on the heating temperature, the time period for thermally treating the synthesized molecular sieve comprising flocculant varies; however, it is preferable to heat the synthesized molecular sieve or wet filtercake comprising one or more flocculant(s) at a temperature in the range of from about 80° C. to about 180° C., preferably from about 90° C. to about 160° C., for a period of about 1 hour to about 24 hours or more, preferably from about 1.5 hours to about 20 hours.

In one embodiment, the synthesized molecular sieve comprising a flocculant and optionally a templating agent, is thermally treated or heat treated to a level such that the LOI of the molecular sieve is in the range of from about 5% to about 50%, preferably from about 10% to about 40%, more preferably from about 15% to about 30%, and most preferably from about 15% to about 20%.

The amount of flocculant introduced to the reactor vessel depends on the quantity of molecular sieve being recovered. In one embodiment, the amount of molecular sieve recovered is the range of from about 100 Kg to about 20,000 Kg or greater, preferably in the range of from 250 Kg to about 20,000 Kg, more preferably from about 500 Kg to about 20,000 Kg, and most preferably from about 1000 Kg to about 20,000 Kg. In another embodiment, the reactor vessel is capable of synthesizing an amount of molecular sieve in one batch or at one time in the range from about 100 Kg to about 20,000 Kg or greater, preferably greater than about 250 Kg to about 20,000 Kg, more preferably from about 500 Kg to about 20,000 Kg, and most preferably from about 1000 Kg to about 20,000 Kg.

Method for Making Molecular Sieve Catalyst Compositions

Once the molecular sieve is synthesized and heat treated as described above, depending on the requirements of the particular conversion process, the molecular sieve is then formulated into a molecular sieve catalyst composition, particularly for commercial use. The molecular sieves synthesized above are made or formulated into molecular sieve catalyst compositions by combining the synthesized molecular sieve(s), after being thermally treated, with a binder, and optionally, but preferably, with a matrix material to form a formulated molecular sieve catalyst composition.

This formulated composition is formed into useful shape and sized particles by well-known techniques such as spray drying, pelletizing, extrusion, and the like, spray drying being the most preferred. It is also preferred that after spray drying for example that the formulated molecular sieve catalyst composition is then calcined.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrate. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrate, a hydroxylated aluminum based sol containing a chloride counter ion, has the general formula of $Al_mO_n(OH)_oCl_p.x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7.12(H_2O)$ as is described in G. M. Wolterman, et al., Stud. Surf. Sci. and Catal., 76, pages 105–144 (1993), which is herein incorporated by reference. In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol AL20DW, available from Nyacol Nano Technologies, Inc., Ashland, Mass.

The synthesized molecular sieves described above, in a preferred embodiment, is combined with a binder and one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, non-active, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. In one embodiment, the matrix material, preferably any of the clays, are subjected to well known modification processes such as calcination and/or acid treatment and/or chemical treatment. In one preferred embodiment, the matrix material is kaolin, particularly kaolin having an average particle size from about 0.1 μm to about 0.6 μm with a $d_{90}$ particle size distribution of less than about 1 μm.

Upon combining the heat treated synthesized molecular sieve and the matrix material, optionally with a binder, in a liquid to form a slurry, mixing, preferably rigorous mixing, is needed to produce a substantially homogeneous mixture containing the heat treated synthesized molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The liquid containing the heat treated synthesized molecular sieve and matrix material, and the optional binder, are in the same or different liquid, and are combined in any order, together, simultaneously, sequentially, or a combination thereof. In the preferred embodiment, the same liquid, preferably water is used.

In one embodiment, the weight ratio of the binder to the molecular sieve is in the range of from about 0.1 to 0.5, more preferably in the range of from 0.11 to 0.48, even more preferably from 0.12 to about 0.45, yet even more preferably from 0.13 to less than 0.45, and most preferably in the range of from 0.15 to about 0.4. See for example U.S. patent application Ser. No. 10/178,455 filed Jun. 24, 2002, which is herein fully incorporated by reference.

The molecular sieve catalyst composition particles contains some water, templating agent or other liquid components, therefore, the weight percents that describe the solid content in the slurry are preferably expressed in terms exclusive of the amount of water, templating agent and/or other liquid contained within the particle. The most preferred condition for measuring solids content is on a calcined basis as, for example, as measured by the LOI procedure discussed above. On a calcined basis, the solid content in the slurry, more specifically, the molecular sieve catalyst composition particles in the slurry, are from about 20 percent by weight to 45 percent by weight molecular sieve, 5 percent by weight to 20 percent by weight binder, and from about 30 percent by weight to 80 percent by weight matrix material. See for example U.S. Patent Application Publication No. US 2003/0018228 published Jan. 23, 2003, which is herein fully incorporated by reference.

In another embodiment, the heat treated molecular sieve is combined with a binder and/or a matrix material forming a slurry such that the pH of the slurry is above or below the isoelectric point of the molecular sieve. Preferably the slurry comprises the molecular sieve, the binder and the matrix material and has a pH different from, above or below, preferably below, the IEP of the molecular sieve, the binder and the matrix material. In an embodiment, the pH of the slurry is in the range of from 2 to 7, preferably from 2.3 to 6.2; the IEP of the molecular sieve is in the range of from 2.5 to less than 7, preferably from about 3.5 to 6.5; the IEP of the binder is greater than 10; and the IEP of the matrix material is less than 2. See PCT Patent Publication WO 03/000412 A1 published Jan. 3, 2003, which is herein fully incorporated by reference.

As the slurry is mixed, the solids in the slurry aggregate preferably to a point where the slurry contains solid molecular sieve catalyst composition particles. It is preferable that these particles are small and have a uniform size distribution such that the $d_{90}$ diameter of these particles is less than 20 μm, preferably less than 15 μm, more preferably less than 10 μm, and most preferably about 7 μm. The $d_{90}$ for purposes of this patent application and appended claims means that 90 percent by volume of the particles in the slurry have a particle diameter lower than the $d_{90}$ value. For the purposes of this definition, the particle size distribution used to define the $d_{90}$ is measured using well known laser scattering techniques using a Honeywell (Microtrac Model 3000 particle size analyzer from Microtrac, Inc., Largo, Fla.).

In one embodiment, the slurry of the synthesized molecular sieve, binder and matrix material is mixed or milled to achieve a sufficiently uniform slurry of sub-particles of the molecular sieve catalyst composition to form a formulation composition that is then fed to a forming unit that produces the molecular sieve catalyst composition or formulated molecular sieve catalyst composition. In a preferred embodiment, the forming unit is a spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, any one or a combination of the slurries described above, more particularly a slurry of the synthesized molecular sieve, matrix material, and binder, is co-fed to the spray dryer with a drying gas with an average inlet temperature ranging from 200° C. to 550° C., and a combined outlet temperature ranging from 100° C. to about 225° C. In an embodiment, the average diameter of the spray dried formed catalyst composition is from about 40 μm to about 300 μm, preferably from about 50 μm to about 250 μm, more preferably from about 50 μm to about 200 μm, and most preferably from about 65 μm to about 90 μm.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomization fluid such as air, steam, flue gas, or any other suitable gas. Generally, the size of the microspheres is controlled to some extent by the solids content of the slurry. However, control of the size of the catalyst composition and its spherical characteristics are controllable by varying the slurry feed properties and conditions of atomization.

Other methods for forming a molecular sieve catalyst composition is described in U.S. Pat. No. 6,509,290 (spray drying using a recycled molecular sieve catalyst composition), which is herein incorporated by reference.

In a preferred embodiment, once the molecular sieve catalyst composition is formed, to further harden and/or activate the formed catalyst composition, the spray dried molecular sieve catalyst composition or formulated molecular sieve catalyst composition is calcined. Typical calcination temperatures are in the range of from about 500° C. to about 800° C., and preferably from about 550° C. to about 700° C., preferably in a calcination environment such as air, nitrogen, helium, flue gas (combustion product lean in oxygen), or any combination thereof. Calcination time is typically dependent on the degree of hardening of the molecular sieve catalyst composition and ranges from about 15 minutes to about 20 hours at a temperature in the range of from 500° C. to 700° C.

In one embodiment, the attrition resistance of a molecular sieve catalyst composition is measured using an Attrition Rate Index (ARI), measured in weight percent catalyst composition attrited per hour. ARI is measured by adding 6.0 g of catalyst composition having a particle size distribution ranging from 53 microns to 125 microns to a hardened steel attrition cup. Approximately 23,700 cc/min of nitrogen gas is bubbled through a water-containing bubbler to humidify the nitrogen. The wet nitrogen passes through the attrition cup, and exits the attrition apparatus through a porous fiber thimble. The flowing nitrogen removes the finer particles, with the larger particles being retained in the cup. The porous fiber thimble separates the fine catalyst particles from the nitrogen that exits through the thimble. The fine particles remaining in the thimble represent the catalyst composition that has broken apart through attrition. The nitrogen flow passing through the attrition cup is maintained for 1 hour. The fines collected in the thimble are removed from the unit. A new thimble is then installed. The catalyst left in the attrition unit is attrited for an additional 3 hours, under the same gas flow and moisture levels. The fines collected in the thimble are recovered. The collection of fine catalyst particles separated by the thimble after the first hour are weighed. The amount in grams of fine particles divided by the original amount of catalyst in grams charged to the attrition cup expressed on per hour basis is the ARI, in weight percent per hour (wt. %/hr). ARI is represented by the formula: ARI=C/(B+C)/D multiplied by 100%, wherein B is weight of catalyst composition left in the cup after the attrition test, C is the weight of collected fine catalyst particles after the first hour of attrition treatment, and D is the duration of treatment in hours after the first hour attrition treatment.

In one embodiment, the molecular sieve catalyst composition or formulated molecular sieve catalyst composition has an ARI less than 10 weight percent per hour, preferably less than 5 weight percent per hour, more preferably less than 2 weight percent per hour, and most preferably less than 1 weight percent per hour.

Process for Using the Molecular Sieve Catalyst Compositions

The molecular sieve catalyst compositions described above are useful in a variety of processes including: cracking, of for example a naphtha feed to light olefin(s) (U.S. Pat. No. 6,300,537) or higher molecular weight (MW) hydrocarbons to lower MW hydrocarbons; hydrocracking, of for example heavy petroleum and/or cyclic feedstock; isomerization, of for example aromatics such as xylene, polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumeme or with long chain olefins; transalkylation, of for example a combination of aromatic and polyalkylaromatic hydrocarbons; dealkylation; hydrodecylization; disproportionation, of for example toluene to make benzene and paraxylene; oligomerization, of for example straight and branched chain olefin(s); and dehydrocyclization.

Preferred processes are conversion processes including: naphtha to highly aromatic mixtures; light olefin(s) to gasoline, distillates and lubricants; oxygenates to olefin(s); light paraffins to olefins and/or aromatics; and unsaturated hydrocarbons (ethylene and/or acetylene) to aldehydes for conversion into alcohols, acids and esters. The most preferred process of the invention is a process directed to the conversion of a feedstock comprising one or more oxygenates to one or more olefin(s).

The molecular sieve catalyst compositions described above are particularly useful in conversion processes of different feedstock. Typically, the feedstock contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene. Nonlimiting examples of olefin monomer(s) include ethylene, propylene, butene-1, pentene-1, 4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition of the invention into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The are many processes used to convert feedstock into olefin(s) including various cracking processes such as steam cracking, thermal regenerative cracking, fluidized bed cracking, fluid catalytic cracking, deep catalytic cracking, and visbreaking. The most preferred process is generally referred to as gas-to-olefins (GTO) or alternatively, oxygenate-to-olefins (OTO) or methanol-to-olefins (MTO). In a MTO or an OTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and *Fluidization Engineering*, D. Kunii and O. Levenspiel, Robert E. Krieger Publishing Company, New York, N.Y. 1977, which are all herein fully incorporated by reference. The preferred reactor type are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

Reactor System

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

The feedstock entering the reactor system is preferably converted, partially or fully, in the first reactor zone into a gaseous effluent that enters the disengaging vessel along with a coked or further coked molecular sieve catalyst composition. In the preferred embodiment, cyclone(s) within the disengaging vessel are designed to separate the molecular sieve catalyst composition, preferably a coked or further coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor. Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference. Other processes for converting an oxygenate to olefin(s) are described in U.S. Pat. No. 5,952,538 (WHSV of at least 20 $hr^{-1}$ and a Temperature Corrected Normalized Methane Selectivity (TCNMS) of less than 0.016), EP-0 642 485 B1 (WHSV is from 0.01 $hr^{-1}$ to about 100 $hr^{-1}$, at a temperature of from about 350° C. to 550° C.), and PCT WO 01/23500 published Apr. 5, 2001 (propane reduction at an average catalyst feedstock exposure of at least 1.0), which are all herein fully incorporated by reference.

The coked molecular sieve catalyst composition is withdrawn from the disengaging vessel, preferably by one or more cyclones(s), and introduced to the regeneration system.

Regeneration System

The regeneration system comprises a regenerator where the coked catalyst composition is contacted with a regeneration medium, preferably a gas containing oxygen, under general regeneration conditions of temperature, pressure and residence time. Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition. By controlling the flow of the regenerated molecular sieve catalyst composition or cooled regenerated molecular sieve catalyst composition from the regeneration system to the reactor system, the optimum level of coke on the molecular sieve catalyst composition entering the reactor is maintained. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336–337), which is herein incorporated by reference.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa). The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

Other regeneration processes are described in U.S. Pat. No. 6,023,005 (coke levels on regenerated catalyst), U.S. Pat. No. 6,245,703 (fresh molecular sieve added to regenerator) and U.S. Pat. No. 6,290,916 (controlling moisture), U.S. patent application Ser. No. 09/587,766 filed Jun. 6, 2000 (cooled regenerated catalyst returned to regenerator), U.S. patent application Ser. No. 09/785,122 filed Feb. 16, 2001 (regenerated catalyst contacted with alcohol), and PCT WO 00/49106 published Aug. 24, 2000 (cooled regenerated catalyst contacted with by-products), which are all herein fully incorporated by reference.

The gaseous effluent is withdrawn from the disengaging system and is passed through a recovery system.

Recovery System

There are many well known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like. Non-limiting examples of these towers, columns, splitters or trains used alone or in combination include one or more of a demethanizer, preferably a high temperature demethanizer, a dethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

In particular with a conversion process of oxygenates into olefin(s) utilizing a molecular sieve catalyst composition the resulting effluent gas typically comprises a majority of ethylene and/or propylene and a minor amount of four carbon and higher carbon number products and other by-products, excluding water. In one embodiment, high purity ethylene and/or high purity propylene is produced by the process of the invention at a rate greater than 4,500 kg per day, preferably greater than 100,000 kg per day, more preferably greater than 500,000 kg per day, even more preferably greater than 1,000,000 kg per day, yet even more preferably greater than 1,500,000 kg per day, still even more preferably greater than 2,000,000 kg per day, and most preferably greater than 2,500,000 kg per day.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system to remove various non-limiting examples of contaminants and by-products include generally polar compounds such as water, alcohols, carboxylic acids, ethers, carbon oxides, ammonia and other nitrogen compounds, chlorides, hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Included in the recovery systems of the invention are reaction systems for converting the products contained within the effluent gas withdrawn from the reactor or converting those products produced as a result of the recovery system utilized. Suitable well known reaction systems as part of the recovery system primarily take lower value products such as the $C_4$ hydrocarbons, butene-1 and butene-2 and convert them to higher value products. Non-limiting examples of these types of reaction systems include U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading $C_3$, $C_4$ and $C_5$ Olefinic Streams*, Pet. & Coal, Vol. 37, No. 4 (1995) (dimerizing or oligomerizing propylene, butylene and pentylene), which are all herein fully incorporated by reference.

Other conversion processes, in particular, a conversion process of an oxygenate to one or more olefin(s) in the presence of a molecular sieve catalyst composition, especially where the molecular sieve is synthesized from a silicon-, phosphorous-, and alumina-source, include those described in for example: U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in effluent gas fed to another reactor) PCT WO 01/60770 published Aug. 23, 2001 and U.S. patent application Ser. No. 09/627,634 filed Jul. 28, 2000 (high pressure), U.S. patent application Ser. No. 09/507,838 filed Feb. 22, 2000 (staged feedstock injection), and U.S. patent application Ser. No. 09/785,409 filed Feb. 16, 2001 (acetone co-fed), which are all herein fully incorporated by reference.

Integrated Processes

In an embodiment, an integrated process is directed to producing light olefin(s) from a hydrocarbon feedstock, preferably a hydrocarbon gas feedstock, more preferably methane and/or ethane. The first step in the process is passing the gaseous feedstock, preferably in combination with a water stream, to a syngas production zone to produce a synthesis gas (syngas) stream. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas. Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fusel oil. The oxygenate containing stream, crude methanol, in the preferred embodiment is passed through a well known purification processes, distillation, separation and fractionation, resulting in a purified oxygenate containing stream, for example, commercial Grade A and AA methanol. The oxygenate containing stream or purified oxygenate containing stream, optionally with one or more diluents, is contacted with one or more molecular sieve catalyst composition described above in any one of the processes described above to produce a variety of prime products, particularly light olefin(s), ethylene and/or propylene. Non-limiting examples of this integrated process is described in EP-B-0 933 345, which is herein fully incorporated by reference. In another more fully integrated process, optionally with the integrated processes described above, olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Light Olefin Usage

The light olefin products, especially the ethylene and the propylene, are useful in polymerization processes that include solution, gas phase, slurry phase and a high pressure processes, or a combinations thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

In preferred embodiment, the integrated process comprises a polymerizing process of one or more olefin(s) in the presence of a polymerization catalyst system in a polymerization reactor to produce one or more polymer products, wherein the one or more olefin(s) having been made by converting an alcohol, particularly methanol, using a molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

EXAMPLES

In order to provide a better understanding of the present invention including representative advantages thereof, the following examples are offered.

LOI and ARI are specified in this patent specification.

Carbon Content Analysis

Molecular sieve catalysts contain organic or carbonaceous materials introduced either during the molecular sieve synthesis step, for example as a template and/or as a flocculant. In order to determine the amount of organic materials present in the molecular sieve catalysts, a small amount of a catalyst sample is used on a carbon analysis instrument, for example, a Carlo Erba EA 1108 Elemental Analyzer, from Carlo-Erba Instruments, Milan, Italy. This Elemental Analyzer determines the amount of carbon dioxide produced during a dynamic flash combustion occurring at greater than 1020° C. The products resulting from the combustion are then analyzed using a chromatograph having a Porapak PQS column and a thermal conductivity detector, after first calibrating the chromatograph with standards of known carbon content. This method allows accurate determination of carbon content of from about 0.01 to 100% of the molecular sieve catalyst samples.

Apparent Bulk Density

Apparent bulk density (ABD) is determined using the following procedure: first weighing a graduated cylinder accurate to 0.1 cc of 25 cc capacity, i.e., a KIMAX gradual cylinder from KAMBLE USA, to record the cylinder weight $W_a$, then pour approximately 25 cc of a spray dried and calcined molecular sieve catalyst composition into the graduated cylinder, tap the cylinder bottom against a lab bench surface at a frequency of 160 to 170 times per minute for 30 seconds to pack the catalyst composition in the cylinder. Record the final weight of the graduated cylinder containing the catalyst, $W_b$, and the volume of the catalyst, $V_c$. ABD is calculated as $(W_b-W_a)/V_c$ in gram per cc. For example, a catalyst composition weighing 15.23 g gives an ABD of 0.78 g/cc {(76.45 g−61.22 g)/1 9.5 cc}. The ABD is always higher than the pour ABD, which is determined by pouring a catalyst composition into a given volume without any packing or compaction.

Prophetic Example A

There are numerous methods well known for making molecular sieves. The following is an example preparation of a molecular sieve, particularly a silicoaluminophosphate molecular sieve. Procedures for making a similar molecular sieve used in the examples below is described in PCT Publication WO 02/070407 published Sep. 12, 2002, which is fully incorporated by reference.

A solution of 33.55 grams of phosphoric acid (85% in water), 32.13 grams of de-mineralized water, and 61.4 grams of a TEAOH solution (35% in water) is put into a glass beaker. To this solution add 3.32 grams of Ludox AS 40 (40% silica) and add 19.85 grams of alumina (Condea Pural SB). This slurry solution, a synthesis mixture, would have a composition expressed as molar ratios:

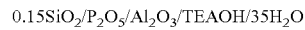

0.15SiO$_2$/P$_2$O$_5$/Al$_2$O$_3$/TEAOH/35H$_2$O

This synthesis mixture would then be mixed until homogeneous and put into a 150 ml stainless steel autoclave. The autoclave would be mounted on a rotating axis in an oven. The axis would be rotated at 60 rpm and the oven would be heated in 8 hours to 175° C. The autoclave should be kept at this temperature for 48 hours.

After the synthesis mixture is preferably allowed to cool, a flocculant would be added. At this point a gradually increasing amount of flocculant would be added until there is detectable settling of the crystals within the vessel as indicated by a qualitative reduction in the solids content at a point relatively high in the vessel when compared to the solids content determined at a point lower in the vessel. Solids determination in this step may be visual by comparing the opacity of two samples at different elevations. After the crystals generally settle to near the bottom of the vessel, the solids-lean liquid upper layer would be removed by decantation or pumping. In a preferred embodiment, additional water would be added and the process repeated as necessary to achieve a qualitatively or near clear liquid above the settled crystals. The settled crystals would then be transferred by pumping to a filter and recoverable for further processing.

Example 1

The molecular sieve catalyst similar to that described in Example A in the form of a wet filtercake was recovered in the presence of a flocculant using on a filter. (Catalyst A). The recovered Catalyst A was then washed with water until the effluent water had a measured conductivity of 6000 μS/cm. The resulting Catalyst A had a LOI of 54.98% and a carbon content on dry basis of 13.87%.

Example 2

A 500 g sample of Catalyst A of Example 1 in the form of a wet filtercake in lumps was placed in a ceramic container to give a bed thickness of 2 cm to 3 cm. Catalyst A in the ceramic container was introduced into an oven that had been preheated to 180° C., and Catalyst A was heat treated at 180° C. for about 3 hours. The circulation rate of air in the oven was at 8 to 10 CFM (Cubic Feet per Minute) (0.23 m$^3$/minute to 0.29 m$^3$/minute). After the heat treatment, Catalyst A had a LOI of 30.34% and a carbon content on dry basis of 13.23%.

Example 3

An amount of 500 g of Catalyst A of Example 1 in the form of a wet filtercake in lumps was placed in a ceramic container to give a bed thickness of 2 cm to 3 cm. Catalyst A in the ceramic container was introduced into an oven that had been preheated to 180° C., and Catalyst A was heat treated at 180° C. for about 15.5 hours. The circulation rate of air in the oven was at 8 to 10 CFM (0.23 m$^3$/minute to 0.29 m$^3$/minute). After the heat treatment, Catalyst A had a LOI of 18.04% and a carbon content on dry basis of 12.69%.

Example 4

A 500 g sample of a Catalyst B wet filtercake, the same as Catalyst A of Example 1 above, except that it was washed in water to give an effluent having a measured conductivity of 1000 μS/cm. Catalyst B in a ceramic container at a bed thickness of 2 cm to 3 cm was introduced into an oven that had been preheated to 120° C., and Catalyst B was heat treated at 120° C. for about 24 hours. The circulation rate of air in the oven was at 8 to 10 CFM (0.23 m$^3$/minute to 0.29 m$^3$/minute). After the heat treatment, Catalyst B had a LOI of 17.66% and a carbon content on dry basis of 12.12%.

Example 5

A 500 g sample of Catalyst B as described in Example 4 in a ceramic container at a bed thickness of 2 cm to 3 cm was introduced into an oven that had been preheated to 180° C., and heat treated at 180° C. for about 96 hours. The circulation rate of air in the oven was at 8 to 10 CFM (0.23 m$^3$/minute to 0.29 m$^3$/minute). After the heat treatment, Catalyst B had a LOI of 17.71% and a carbon content on dry basis of 12.42%.

Example 6

A final slurry was prepared using Catalyst A treated in the same manner as in Example 3. The final slurry was prepared by: (I) adding 410 g of the heat treated molecular sieve, Catalyst A, to 882.3 g of deionized water, and mixing this slurry using a Yamato 4000D mixer (Yamato Scientific America Inc., Orangeburg, N.Y.) at 700 RPM for 10 minutes. This slurry having a pH of 5.47 at 26.6° C., was then mixed using a Silverson high-shear mixer at 6000 RPM for 3 minutes. The resulting slurry of this Step I had a pH of 4.50 at 30.5° C.; (II) a 270.4 g sample of Reheis MicroDry aluminum chlorohydrate (ACH), a binder, (available from Reheis Chemical, Berkeley Heights, N.J.) was then added to the resulting slurry from Step I above, and then mixed at 700 RPM for 10 minutes in the Yamato 4000D mixer. This slurry having a pH of 3.58 at 30.6° C. was then mixed using a Silverson high shear mixer at 6000 RPM for 3 minutes. The resulting slurry of Step II after this mixing step had a pH of 3.53 at 32.1° C.; and (III) a 437.4 g sample of Hydrite UF kaolin clay, a matrix material, (available from Imerys, Roswell, Ga.), was added to the resulting slurry of Step II, and mixed at 700 RPM using the Yamato 4000D mixer for 10 minutes. This slurry having a pH of 3.59 at 30.6° C. was then mixed using the Silverson high-shear mixer at 6000 RPM for 3 minutes. This final slurry of Step III had a pH of 3.50 at 32° C., and a viscosity measured using a Brookfield viscometer and using a #3 spindle of 1460 cP measured at 23° C. Also, this final slurry of Step III contained 42.02% solids of which 40% being the Catalyst A, the molecular sieve, 15.9% being alumina derived from the ACH, the binder, and 44.1% kaolin clay, the matrix material.

The final slurry of Step III above was spray dried using a Yamato DL-41 spray dryer (Yamato Scientific America, Orangeburg, N.Y.) under standard spray drying conditions to give a formulated molecular sieve catalyst composition, that was then calcined in a muffle furnace at 650° C. for 2 hrs. The attrition rate index of the calcined molecular sieve catalyst composition was measured at 0.82%/hr, and had an ABD of 0.86 g/cc.

Example 7

A final slurry was prepared using Catalyst A treated in the same manner as in Example 2. The final slurry was prepared by: (1) adding 198.6 g of the heat treated molecular sieve, Catalyst A, to 298.0 g of deionized water, and mixing this slurry using a Yamato 4000D mixer (Yamato Scientific America Inc., Orangeburg, N.Y.) at 700 RPM for 10 minutes. This slurry having a pH of 5.77 at 23.9° C., was then mixed using a Silverson high-shear mixer at 6000 RPM for 3 minutes. The resulting slurry of this Step I had a pH of 6.19 at 29.5° C.; (II) a 115.9 g sample of Reheis MicroDry aluminum chlorohydrate (ACH), a binder, (available from Reheis Chemical, Berkeley Heights, N.J.) was then added to the resulting slurry from Step I above, and then mixed at 700 RPM for 10 minutes in the Yamato 4000D mixer. This slurry having a pH of 3.54 at 29° C. was then mixed using a Silverson high shear mixer at 6000 RPM for 3 minutes. The resulting slurry of Step II after this mixing step had a pH of 3.44 at 32.5° C.; and (III) a 187.5 g sample of Hydrite UF kaolin clay, a matrix material, (available from Imerys, Roswell, Ga.), was added to the resulting slurry of Step II, and mixed at 700 RPM using the Yamato 4000D mixer for 10 minutes. This slurry having a pH of 3.59 at 31.3° C. was then mixed using the Silverson high-shear mixer at 6000 RPM for 3 minutes. This final slurry of Step III had a pH of 3.05 at 48.9° C., and a viscosity measured using a Brookfield viscometer and using a #3 spindle of 9130 cP measured at 23° C. Also, this final slurry of Step III contained 44.19% solids of which 40% being the Catalyst A, the molecular sieve, 15.9% being alumina derived from the ACH, the binder, and 44.1% kaolin clay, the matrix material.

The final slurry of Step III above was spray dried using a Yamato DL-41 spray dryer (Yamato Scientific America, Orangeburg, N.Y.) under standard spray drying conditions to give a formulated molecular sieve catalyst composition, that was then calcined in a muffle furnace at 650° C. for 2 hrs. The attrition rate index of the calcined molecular sieve catalyst composition was measured at 0.81%/hr, and had an ABD of 0.84 g/cc.

Example 8

A final slurry was prepared using Catalyst A treated in the same manner as in Example 1. The final slurry was prepared by: (I) adding 263.0 g of the heat treated molecular sieve, Catalyst A, to 287.6 g of deionized water, and mixing this slurry using a Yamato 4000D mixer (Yamato Scientific America Inc., Orangeburg, N.Y.) at 700 RPM for 10 minutes. This slurry having a pH of 6.66 at 22.8° C., was then mixed using a Silverson high-shear mixer at 6000 RPM for 3 minutes. The resulting slurry of this Step I had a pH of 6.7 at 27.6° C.; (II) a 95.3 g sample of Reheis MicroDry aluminum chlorohydrate (ACH), a binder, (available from Reheis Chemical, Berkeley Heights, N.J.) was then added to the resulting slurry from Step I above, and then mixed at 700 RPM for 10 minutes in the Yamato 4000D mixer. This slurry having a pH of 4.01 at 28.5° C. was then mixed using a Silverson high shear mixer at 6000 RPM for 3 minutes. The resulting slurry of Step II after this mixing step had a pH of 4.00 at 31.8° C.; and (I) a 154.1 g sample of Hydrite UF kaolin clay, a matrix material, (available from Imerys, Roswell, Ga.), was added to the resulting slurry of Step II, and mixed at 700 RPM using the Yamato 4000D mixer for 10 minutes. This slurry having a pH of 4.10 at 30.5° C. was then mixed using the Silverson high-shear mixer at 6000 RPM for 3 minutes. This final slurry of Step III had a pH of 4.07 at 32.2° C., and a viscosity measured using a Brookfield viscometer and using a #3 spindle of 6790 cP measured at 23° C. Also, this final slurry of Step III contained 36.95% solids of which 40% being the Catalyst A, the molecular sieve, 15.9% being alumina derived from the ACH, the binder, and 44.1% kaolin clay, the matrix material.

The final slurry of Step III above was spray dried using a Yamato DL-41 spray dryer (Yamato Scientific America, Orangeburg, N.Y.) under standard spray drying conditions to give a formulated molecular sieve catalyst composition, that was then calcined in a muffle furnace at 650° C. for 2 hrs. The attrition rate index of the calcined molecular sieve catalyst composition was measured at 1.21%/hr, and had an ABD of 0.67 g/cc.

While the present invention has been described and illustrated by reference to particular embodiments, those of ordinary skill in the art will appreciate that the invention lends itself to variations not necessarily illustrated herein. For example, it is contemplated that the molecular sieve catalyst composition is useful in the inter-conversion of olefin(s), oxygenate to gasoline conversions reactions, malaeic anhydride, phthalic anhydride and acrylonitrile formulation, vapor phase methanol synthesis, and various Fischer Tropsch reactions. It is further contemplated that a plug flow, fixed bed or fluidized bed process are used in combination, particularly in different reaction zones within a single or multiple reactor system. It is also contemplated the molecular sieve catalyst compositions described herein are useful as absorbents, adsorbents, gas separators, detergents, water purifiers, and other various uses such as agriculture and horticulture. Additionally contemplated molecular sieve catalyst compositions include one or more other molecular sieves in combination. For this reason, then, reference should be made solely to the appended claims for purposes of determining the true scope of the present invention.

We claim:

1. A method for synthesizing a molecular sieve, the method comprising the steps of:
   (a) crystallizing the molecular sieve in a slurry in a reaction vessel, the slurry comprising a silicon source, an aluminum source, a phosphorous source, and a templating agent;
   (b) settling the molecular sieve in a reaction vessel by introducing a flocculant to the slurry;
   (c) recovering the molecular sieve; and
   (d) heat treating the recovered molecular sieve at a temperature in the range of from about 50° C. to about 250° C.

2. The method of claim 1 wherein the in step (c), the molecular sieve is recovered by filtration.

3. The method of claim 1 wherein the amount of molecular sieve recovered is greater than 250 Kg.

4. The method of claim 1 wherein in step (d) the molecular sieve is heated to a temperature in the range of from 80° C. to 150° C.

5. The method of claim 1 wherein the molecular sieve after step (d) has a carbon content in the range of from 0.1% to about 50%.

6. The method of claim 1 wherein the molecular sieve after step (d) has a LOI in the range of from 10% to 50%.

7. The method of claim 1 wherein the molecular sieve is combined with a matrix material, and optionally a binder to form a formulated catalyst composition.

8. The method of claim 7 wherein the formulated molecular sieve catalyst composition is spray dried.

9. The method of claim 8 wherein the formulated molecular sieve catalyst composition is calcined.

10. A method for formulating a molecular sieve catalyst composition, the method comprising the steps of:
(A) synthesizing a molecular sieve selected from one or more of the group consisting of: a silicoaluminophosphate, an aluminophosphate, a CHA framework-type molecular sieve, an AEI framework-type molecular sieve and a CHA and AEI intergrowth or mixed framework-type molecular sieve, in a reaction vessel, the method comprising the steps of:
 (a) crystallizing the molecular sieve in a synthesis mixture;
 (b) settling the molecular sieve in a reaction vessel by introducing a flocculant to the synthesis mixture;
 (c) recovering the molecular sieve;
 (d) thermally treating the molecular sieve at a temperature of from about 50° C. to about 250° C.; and
(B) combining the thermally treated molecular sieve with a binder and a matrix material to form the molecular sieve catalyst composition.

11. The method of claim 10 wherein the molecular sieve in step (c) is recovered by filtering the synthesis mixture.

12. The method of claim 10 wherein prior to step (c) a portion of a liquid in the synthesis mixture is separated from the molecular sieve, and additional flocculant and/or additional liquid, is introduced to the synthesis mixture.

13. The method of claim 10 wherein the reactor vessel is capable of producing greater than 250 Kg in one batch.

14. The method of claim 10 wherein in step (B) the molecular sieve catalyst composition is spray dried to form a spray dried molecular sieve catalyst composition.

15. The method of claim 14 wherein the spray dried molecular sieve catalyst composition is calcined.

16. The method of claim 10 wherein the molecular sieve in step (d) is thermally treated at a temperature in the range of from 80° C. to 150° C.

17. The method of claim 10 wherein the molecular sieve after step (d) has a carbon content in the range of from 0.1% to about 50%.

18. The method of claim 10 wherein the molecular sieve after step (d) has a LOI in the range of from 10% to 50%.

* * * * *